United States Patent [19]
Tsurumaki et al.

[11] Patent Number: 5,177,778
[45] Date of Patent: Jan. 5, 1993

[54] X-RAY RADIOGRAPHING APPARATUS

[75] Inventors: Haruyuki Tsurumaki, Nishinasuno; Hisanori Nakada, Ujiie, both of Japan

[73] Assignee: Kabushiki Kaisha Toshiba, Kawasaki, Japan

[21] Appl. No.: 854,893

[22] Filed: Mar. 20, 1992

[30] Foreign Application Priority Data

Mar. 22, 1991 [JP] Japan .................................. 3-058494

[51] Int. Cl.$^5$ ............................................. H05G 1/54
[52] U.S. Cl. .................................... 378/117; 378/115; 378/197
[58] Field of Search ................................ 378/195–198, 378/4, 98, 117, 114, 115, 116

[56] References Cited

U.S. PATENT DOCUMENTS

4,969,170 11/1990 Kikuchi et al. ..................... 378/114
4,991,193 2/1991 Cecil et al. ............................ 378/4

Primary Examiner—Janice A. Howell
Assistant Examiner—Don Wong
Attorney, Agent, or Firm—Oblon, Spivak, McClelland, Maier & Neustadt

[57] ABSTRACT

An X-ray radiographing apparatus is provided with an interlock mechanism to avoid mutual interference of movable elements such as an X-ray unit, a compression cone, a table, a tabletop and a spot-film device. When a judging element judges, in response to information outputted from a position detecting element of the movable elements and switches operated by an operator, that interlock should be done, an interlocking element is worked, and then a teaching unit is worked. Thus, the interlocked state itself and how to unlock from the interlocked state can be taught to the operator with graphic images by the teaching unit.

13 Claims, 8 Drawing Sheets

X-RAY RADIOGRAPHING APPARATUS

BACKGROUND OF THE INVENTION

The present invention relates to an X-ray radiographing apparatus, and more particularly to the X-ray radiographing apparatus having an interlock mechanism.

An X-ray radiographing apparatus is provided with an interlock mechanism which functions when predetermined prohibited operations are designated. In case the interlock mechanism is worked, it is necessary to teach an operator the interlocked state using, for example, a monitor of the apparatus.

Conventional teaching mechanisms against the interlocked state have been adopting two ways. One way is lighting of specified lamps which can show a simplified figure illustrating, for example, an interlocked states against a patient's table or an X-ray exposure system. The second way is to display messages consisting of only characters, saying for example "Compression cone is under setting. Tabletop and spot-film device can not be operated. Please park compression cone." These messages usually includes prohibited functions and unlock methods.

The above-mentioned lamps having figures give an operator recognition of interlocked states. However, the lamps may not give appropriate unlock methods. Then, operation efficiency depends on the operator's operation ability, and a fast unlock of the interlocked state requires sometimes skill of an operator. On the other hand, the above message totally consisting of charactors could not be understood at a glance by an operator.

SUMMARY OF THE INVENTION

Accordingly, it is a primary object of the present invention to provide an X-ray radiographing apparatus able to display an easily recognizable unlock way from an interlocked state as well as display the interlocked state.

It is a further object of the present invention to provide an X-ray radiographing apparatus able to display a moved portion for unlocking and an unlock direction by graphic images.

It is a still further object of the present invention to provide an X-ray radiographing apparatus able to distinguish graphic images of a moved portion for unlocking and unlock direction in entire graphic image information.

These and other objects can be achieved according to the present invention, in one aspect by providing, an X-ray radiographing apparatus in which at least one movable element is disposed to be moved for X-ray radiographing in response to commands from a switch used by an operator, the X-ray radiographing apparatus comprising an element for detecting positions of said movable element; an element for judging whether or not the movable element is positioned in a predetermined interlock range in response to signals from the switch and the detecting element; an element for interlocking the movable element when judgement by the judging element shows that the movable element is positioned in the interlock range; a unit for teaching the operator an interlocked state of the movable element and how to unlock the interlocked state with graphic images, when the interlocking element begins working.

Preferably, the teaching unit comprises an element for deciding an unlock direction of the movable element from the interlocked state when the interlocking element begins working, an element for converting the unlock direction decided by the deciding element to a corresponding graphic data, an element for generating a graphic data showing the interlocked state of the movable element, and an element for displaying combined graphic images corresponding to the graphic data supplied by the converting and generating elements.

It is preferred that the teaching unit comprises an element for deciding an unlock direction of the movable element from the interlocked state when the interlocking element begins working, an element for converting the unlock direction decided by the deciding element to a correspoding graphic data, a first element for generating graphic data showing the interlocked state of the movable element, a second element for generating graphic date showing an entire perspective view of the X-ray radiographing apparatus, and an element for displaying combined graphic images corresponding to the graphic data supplied by the converting element and the first and second generating elements.

As a result, the operator can learn easily the unlocked state of the apparatus, and can learn at a glance that which moved element should be operated in which way.

In another aspect according to the present invention, there is also provided an X-ray radiographing apparatus, further comprising an element for giving different colors to the graphic images in response to the graphic data generated by the first and second generating elements. Preferably, the color giving element is formed so as to give a same color to the graphic images in response to the graphic data generated by the converting element and the first generating element.

According to the above color giving element, the operator is able to distinguish more easily not only the movable element for unlocking but unlock direction from the entire graphic information.

BRIEF DESCRIPTIONS OF THE DRAWINGS

The accompanying drawings which are incorporated in and constitute a part of this specification, illustrate embodiments of the present invention and, together with the description, serve to explain the principles of the present invention; in which.

DESCRIPTION OF THE PREFERRED EMBODIMENTS

A first embodiment of an X-ray radiographing apparatus in accordance with the present invention will now be described with reference to FIG. 1 to FIG. 7.

Figure 1:
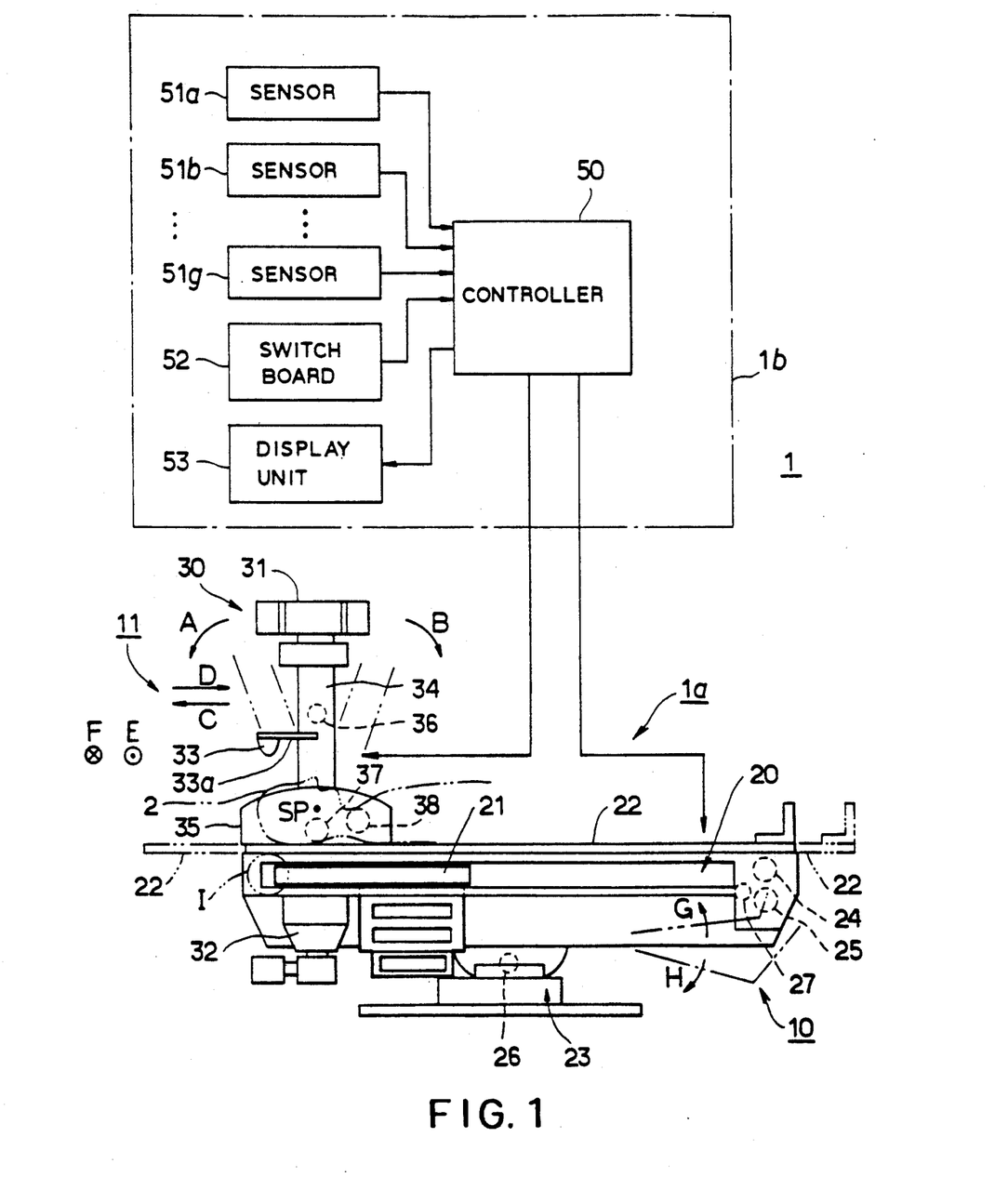
FIG. 1 is a schematic view of an X-ray radiographing apparatus according to a first embodiment of the present invention.

The X-ray radiographing apparatus 1, as shown in FIG. 1, is provided with a radiographing portion 1a and a control portion 1b controlling the radiographing portion 1a. In this apparatus 1, directions pointing upward and downward, rightward and leftward etc. are defined as being such that an origin of the direction system is centered on a patient 2 to be laid down on the table later described.

The radiographing portion 1a comprises a table system and an X-ray exposure system 11.

The table system 10 has a table 20 which contains a spot-film device 21 and a tabletop 22 formed slidably on a topside of the table 20. A patient 2 may lies down on the tabletop 22. The table 20 is installed on a base unit 23 such that the whole table 20 can rise from its horizontal or further tilted position up to its vertical position, and vice versa.

In the table 20, there is provided driving mechanisms which can drive the tabletop 22 and the table 20 in different directions. These driving mechanisms include a tabletop up-down driving mechanism in which a driving motor 24 is disposed as a driving source, a tabletop right-left driving mechanism in which a driving motor 25 is disposed as a driving source, a table tilt driving mechanism in which a driving motor 26 is disposed as a driving source, and a spot-film device driving mechanism in which a driving motor 27 is disposed as a driving source. The driving motors 24 to 27 represent their driving mechanisms, and receive control signals from the control portion 1b, respectively.

Thus, as the driving motor 24 begins to rotate, the tabletop 22 can be moved in the up direction C or down direction D through the tabletop up-down driving mechanism. In the same way, as the driving motor 25 starts, the tabletop 22 can be moved in the right direction E or left direction F through the tabletop right-left driving mechanism. As the motor 26 starts, the tabletop 22 can be moved in the rising direction H or lying direction G. Moreover, the rotation of the driving motor 27 permits moving of the spot-film device 21 in the up or down direction C or D on spot radiography.

The X-ray exposure system 11 comprises an X-ray unit 30 having an X-ray tube 31 and an X-ray detector 32, a compression cone 33, and different driving mechanisms which can move those X-ray unit 30 and compression cone 33.

The X-ray tube 31 is supported over the tabletop 22 by a pillar 34 extending in frong (upward in FIG. 1) from supporting member 35. The X-ray detector 32 is supported under the table 20 by the supporting member 35, being positioned for the X-ray tube 31 through the table 20 and the tabletop 22. X-ray films in the spot-film device 21 can be traveled to a space between the tabletop 22 and the X-ray detector 32 for spot radiography.

The compression cone 33 is disposed on the pillar 34 with a cone arm 33a supported by the pillar 34. The cone arm 33a is designed to be able to extend and shorten its length.

Among the driving mechanisms, there are provided an X-ray tube tilting mechanism in which a driving motor 37 is disposed, an X-ray tube moving mechanism in which a driving motor 38 is arranged, and a compression cone moving mechanism in which a driving motor 39 is arranged. The driving motors 37 to 39 represent their driving mechanisms and receive control signals from the control portion 1b, respectively.

Thus, the rotation of the driving motor 37 allows the pillar 34 to tilt, around a supporting point SP, in an obleque-head side A or an oblique-foot side B. The rotation of the driving motor 38 also allows the X-ray tube 30 and the X-ray detector 31 to move simultaneously in the up direction C or in the down direction D. Moreover, the rotation of the driving motor 39, under parking control of the control portion 1b, permits the cone arm 33a of the compression cone 33 to move away from the patient 2, and vice versa.

Figure 2:
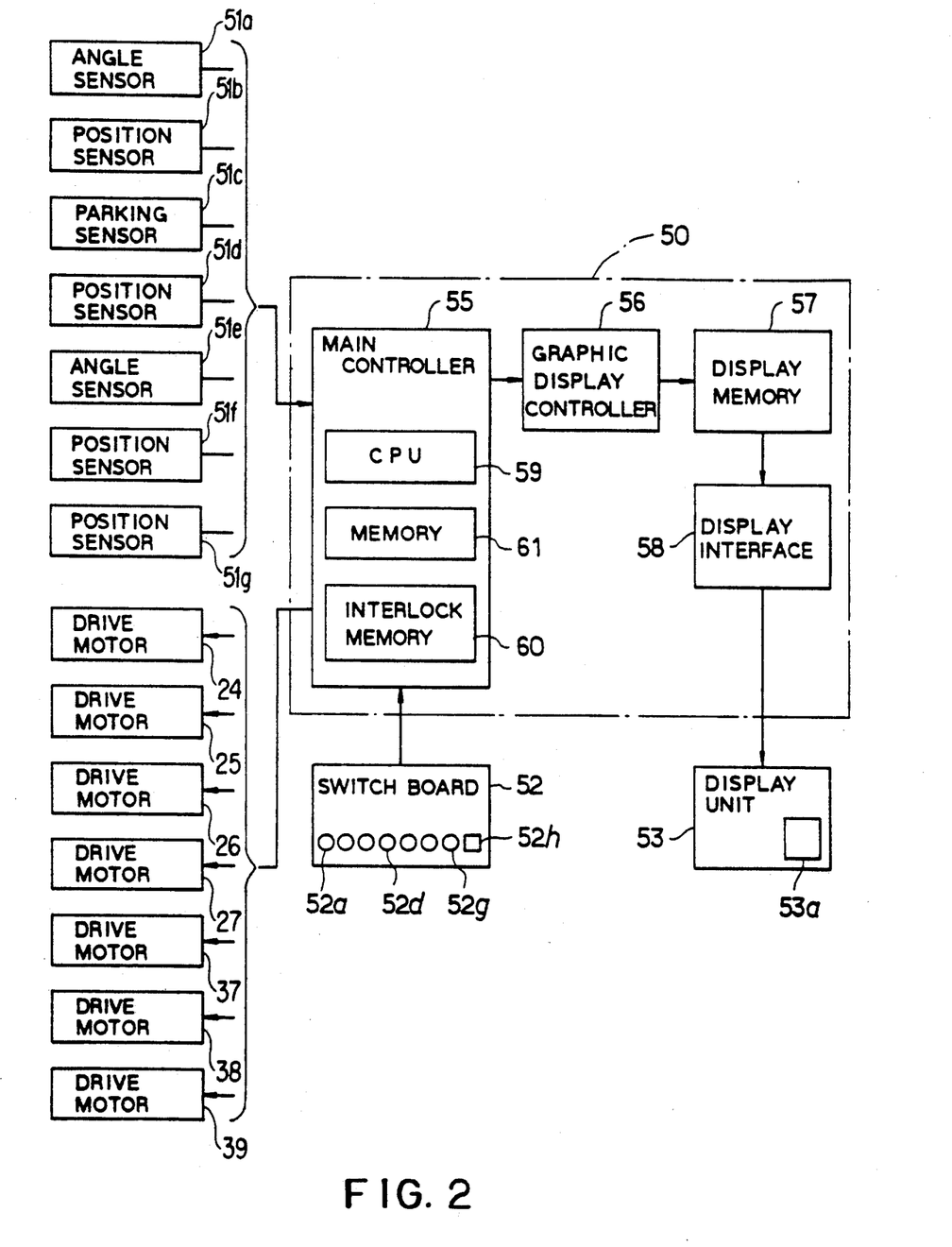
FIG. 2 is a block diagram of a control portion in FIG. 1.

On the other hand, the above-mentioned control portion 1b is provided with a controller 50 for controlling the entire apparatus 1, position sensors 51a to 51g for detecting positions and angles of the movable elements (i.e. the table 20, the tabletop 22, the spot-film device 21, the X-ray unit 30, the compression cone 33) in the table system 10 and the X-ray exposure system 11, a switch board 52 used by an operator, and a display unit 53 for displaying various information including interlock information.

The position sensors are formed by devices such as a photocoupler and a potentiometer. In the various position sensors 51a to 51g, the X-ray tube angle sensor 51a is assigned to detect tilt angles of the X-ray tube 30 in the oblique-head or oblique-foot side A or B, the X-ray unit position sensor 51b to detect positions Of the X-ray unit 30 in the up or down direction C or D, the parking sensor 51c to detect if the compression cone 33 is parked, the spot-film device position sensor 51d to detect positions of the spot-film device 21 in the up or down direction C or D. Furthermore, the table angle sensor 51e is assigned for detecting tilt angles of the table 20 in the rising or lying direction H or G, the tabletop position sensor 51f for detecting positions of the tabletop 22 in the right or left direction E or F, and the tabletop position sensor 51g for detecting positions Of the tabletop 22 in the up or down direction C or D. The detected signals by the position sensors 51a to 51g are all supplied to the controller 50.

The switch board 52, as shown in FIG. 2, has various operating switchs 52a to 52h, each of them having its neutral position; the operating switch 52a is for tilting the X-ray tube 31, the operating switch 52b for moving the X-ray unit 30, the operating switch 52c for moving the compression cone 33, the operating switch 52d for positioning the spot-film device 21, the operating switch 52e for tilting the table 20, the operating switch 52f and 52g for moving the tabletop 22 in the right or left direction and in the up or down direction, and the operating switch 52h for selecting radiographic formats. The outputted switch signals are to be given to the controller 50.

Figure 3:
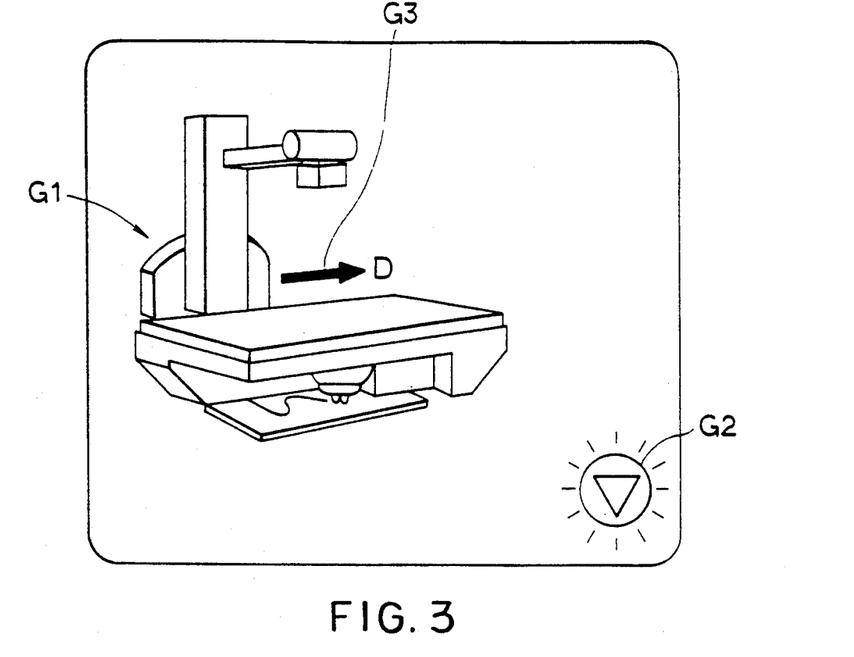
FIGS. 3 and 4 are illustrations of examples of graphic interlock information displayed on a monitor in the first embodiment, respectively.
Figure 4:
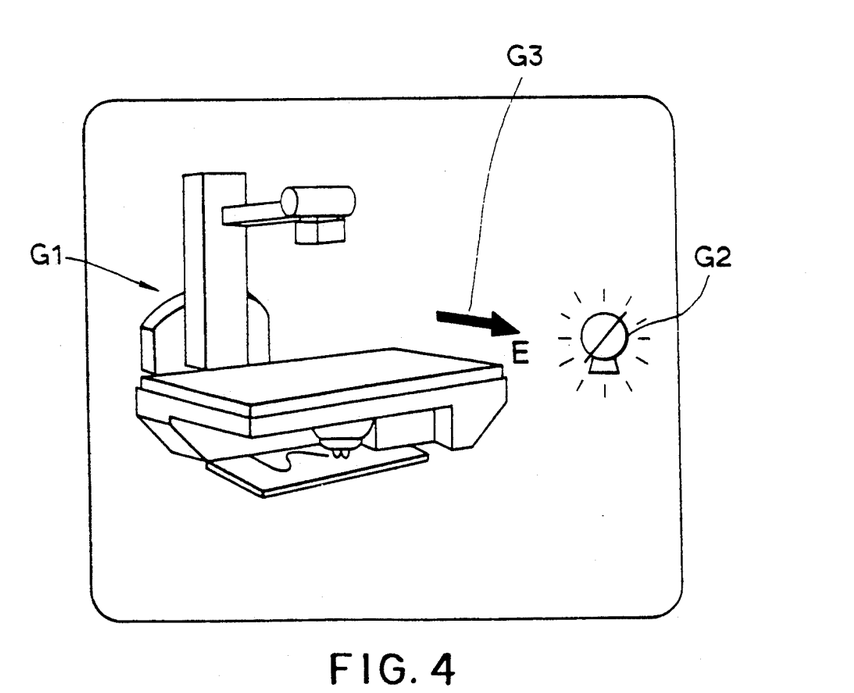

The controller 50, as shown in FIG. 2, comprises a main controller 55, a graphic display controller 56, a display memory 57, and a display interface 58. The main controller 55 comprises a CPU(Central Processing Unit) 59 processing procedures shown in FIGS. 5 to 7 for entire control and an interlock memory 60 storing interlock information. This interlock information includes interlock ranges showing that predetermined interlocks should be operated and graphic information such as shown in FIGS. 3 and 4. In the main controller 55, there is also provided a memory 61 as a RAM and a ROM.

The main controller 55 is to receive the switch signals from the operating switchs 52a to 52h and the position signals from the position sensor 51a to 51g. The main controller 55 can supply drive signals to the motors 24 to 27 and 37 to 39 representing their driving mechanisms, respectively, in the processing according to the procedures in FIGS. 5 to 7.

The graphic display controller 56 is provided for commanding graphic display of interlock information under control of the main controller 55. The display memory 57 is provided for storing temporarily the graphic interlock information outputted from the graphic display controller 56. The display interface 58 is provided for reading out the graphic interlock information from the display memory 57 and supplying it to the display unit 53. The display unit 53 contains a monitor 53a able to display the graphic interlock information through electroluminescence technique.

The above-mentioned graphic interlock information, memorized as graphic data in the interlock memory 60 under normal working condition, can be visualized as shown in FIGS. 3 or 4 on the display unit 53, for instance. In FIGS. 3 and 4, the each graphic interlock information is made up of an entire perspective image G1 showing an outer perspective view of this X-ray radiographing apparatus 1, an interlock-alarming image G2 which is a symbolized figure to show an interlocked state about the table portion 10 (refer to FIG. 3) or about the X-ray exposure system 11 (refer to FIG. 4), and an unlock direction image G3 consisting of an arrow and an abbreviated letter which teaches an operator the unlock direction to unlock the apparatus I from its interlocked state.

In this embodiment, the operating switches 52a to 52h form a switch means of the present invention. The sensors 51a to 51g form a position detecting means of the present invention. Further, the combination of the graphic display controller 56, the display memory 57, the display interface 58, and the display unit 53 constitutes a displaying means of the present invention. On the other hand, the main controller 55 includes a judging means, a deciding means, a converting means, a graphic data generating means (a first and a second generating means included), and a color giving means of the present invention. Moreover, the main controller 50 includes a part of a interlocking means and a part of a teaching means of the present invention.

Then, operation of the controller 50 will now be described with reference to FIGS. 5 to 7.

Figure 5:
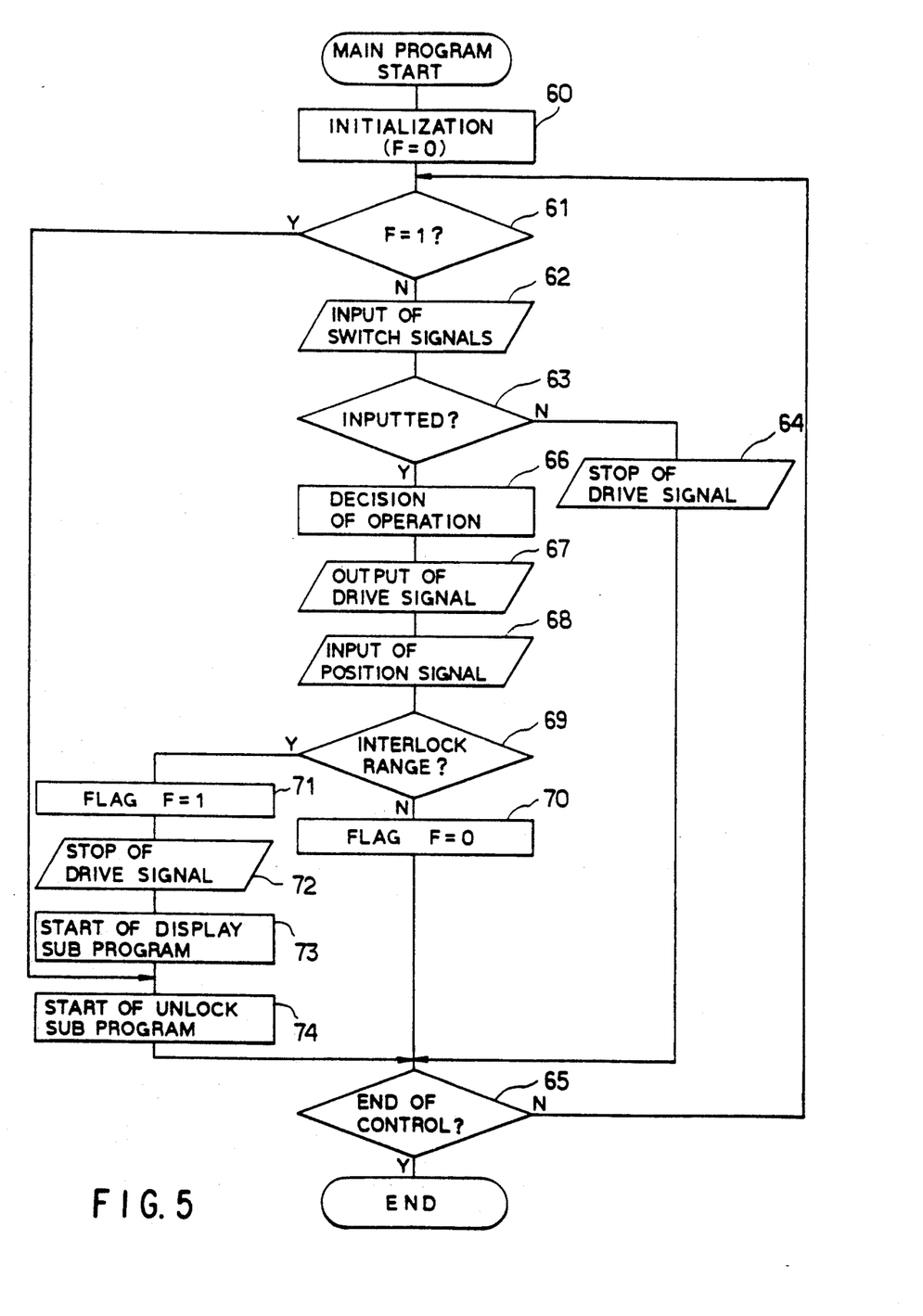
FIGS. 5 to 7 are flowcharts performed by controller in the first embodiment, respectively.

FIG. 5 shows a main program performed by the CPU 59 of the main controller 55. At step 60 in FIG. 5, the CPU 59 performs predetermined initialization including zero setting of a flag F. The flag F shows conditions of this apparatus 1, a normal working state as F=0 and an interlocked state as F=1. In subsequent step 61, the CPU 59 judges whether the flag F=0 or not.

At this Step 61, as the CPU 59 judges the flag F to be F=1, the CPU 59 will then proceed to Steps 62 and 63.

At Step 62, switch signals from the operating switchs 52a to 52h are taken in by the CPU 59. At Step 63, whether the switch signals are live or not is judged. In other words, the CPU 59 is able to recognize that the operating switchs 52a to 52g are in neutral or not and the operating switch 52h is operated or not. Accordingly, when the judgement at Step 63 is NO (i.e. the operating switches 52a to 52g are still in their neutral positions and the operating switch 52h is not operated), the CPU 59 stops or keeps stopping to supply drive signals to the driving motors 24 to 27 and 37 to 39 at Step 64.

After the processing at Step 64, the CPU 59 decides whether the whole control of the apparatus 1 should be ended, according to an instruction of the operator through the switch board 52. The decision of continuing the processing (i.e. NO at Step 65) permits the CPU 59 to repeat the processing from the above-mentioned Step 61.

However, when the judgement at Step 63 is YES (i.e. one of the operating switches 52a to 52g is moved from its neutral position or switch 52h is operated), processes of Steps 66 to 69 will be followed one after another.

At Step 66, the operator's instruction is decoded out from the input switch signal. That is, it can be specified what sort of instruction is given by the operator. Then, at Step 67, a drive signal corresponding to the specified operation is supplied from the main controller 55 to the driving motor 24 (to 27) or 37 (to 39). As a result, the designated driving motor 24 (to 27) or 37 (to 39) starts rotating in a given direction, a designated driving mechanism working.

At Step 68, in order to examine an interlocked state of the apparatus 1, the CPU 59 will take in switch signals of the relevant Operating switchs 52a to 52h to the instruction given by the operator.

Then at Step 69, if the table 20, the tabletop 22, the spot-film device 21, the X-ray unit 30 or the compression cone 33 (i.e. movable elements) is positioned in a predetermined interlock range is judged, in addition to decision of prohibited functions, by the CPU 59. If NO (i.e. the position is not present in the interlock range) at Step 69, the flag F will be assigned to be zero (F=0) at next Step 70, the flag F showing that any interlock is not worked.

On the other hand, when the answer YES (i.e. the position came into the predetermined interlock range) is decided at Step 69, the processing will proceed to next Step 71. At this Step 71, the flag F is assigned to 1 (F=1), showing that one of the movable elements is under interlocked state.

Then, the processes of Steps 72 to 74 will be followed in turn. At Step 72, the drive signal which have been sent so far is turned off to stop the rotation of the designated driving motor 24 (to 27) or 37 (to 39), resulting in that movement of one of the movable elements is interlocked. In the Step 72, a command for stopping the X-ray tube 31 from irradiating X-rays is included.

Figure 6:
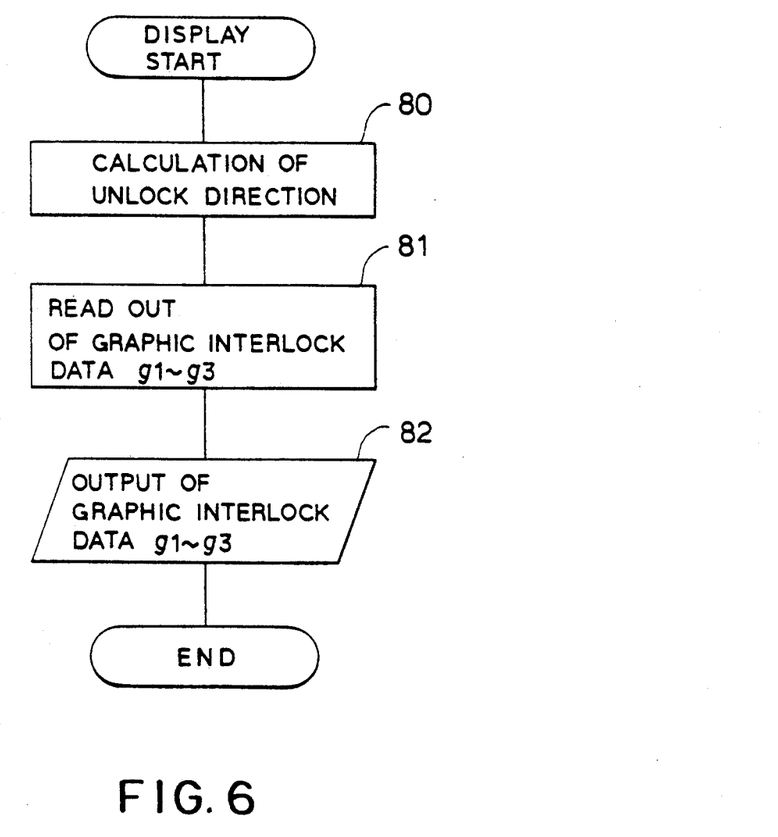

At Step 73, the CPU 59 initiates to start a display sub-program represented in FIG. 6. Subsequently, at Step 74, the CPU 59 initiates to start an unlock sub-program represented in FIG. 7. Then Step 65 will be followed again.

By the way, at the above-mentioned Step 61, the judgement that the flag F equals to 1 (F=1) makes the processing to jump to Step 74, since one of the movable elements has already been under interlocked state.

Now, the display sub-program will be described based on to FIG. 6. At Step 80 of FIG. 6, according to the kind of operation found by the processing at Step 66 of FIG. 5, the CPU 59 calculates an unlock direction which shows a release way from the unlocked state. Then, at Step 81, the CPU 59 gains access to the graphic interlock data g1 to g3 memorized in the interlock memory 60 and takes out a corresponding group of the graphic interlock data g1 to g3. Finally, at Step 82, the taken-in graphic interlock data g1 to g3 will be supplied to the graphic display controller 56.

The graphic display controller 56 thus supplies the display memory 57 with the given graphic interlock data g1 to g3, and write them in a predetermined area of the display memory 57. In response to this writing, the display interface 58 reads out the graphic interlock data g1 to g3 from the display memory 57 and send them to the display unit 53. Accordingly, the graphic interlock images G1 to G3 will be appeared on the monitor 53a, such as shown in FIG. 3 or 4.

Moreover, the unlock sub-program shown in FIG. 7 will be explained. At Step 90 in FIG. 7, the CPU 59 tries to receive the corresponding switch signal to the interlocked state from the switch board 52. Then, at next Step 91, whether the operator operates the operating switches 52a to 52h is judged by examining the switch signal received. If judging that the designated operating switch 52a (to 52g) is returned to its neutral or the operating switch 52h is selected properly under the interlocked state at Step 91 (YES), the processing of the CPU 59 will go to Step 92 to give the graphic display controller 56 a command of turning off the interlock-alarming image G2 only. Then, the graphic display controller 56 eliminates the graphic data g2 only in the display memory 57 to turn off the interlock-alarming image G2 on the monitor 53a.

On the other hand, in case judgement that the operating switch 52a (to 52g) is operated or the operating switch 52h is selected so as not to be unlocked by itself at Step 91 (NO), the same processes as the previously explained Steps 66 and 67 are carried out each at Steps 93 and 94. Thus, the CPU 59 tries to judge whether the operator moved the operating switch 52a (to 52h) toward a position which can unlock the interlocked state. At this Step 94, judgement of NO (i.e. the unlock operation still not given) lead to Step 95 in order to generate a command of turning on the interlock-alarming image G2 again. However, judgement of YES (i.e. the unlock operation given) at Step 94 will be followed by Steps 96 to 98 in turn.

At Step 96, the CPU 59 sends the drive signal to certain designated driving motor 24 (to 27) or 37 (to 39) disposed in the table system 10 or the X-ray exposure system 11, the designated driving motor rotating so as to unlock the interlocked state. In the Step 96, a process for starting working the X-ray tube 31 is included. At Step 97, the relevant position signals of the position sensors 51a to 51g are taken in. At Step 98' by referring to the taken-in position signals, the position of one of the movable elements is examined to see that its position comes off the interlock range. At Step 98, if found that the interlocked state still remains, the processing will be returned to the main program described above. To the contrary, at Step 98, as recognized that the interlocked state is unlocked, processes of Steps 99 and 100 will be followed.

At Step 99, the CPU 59 assigns again the flag F zero (F=0) to show the unlocked state, that is, a return to the normal working state. Subsequently, at Step 100, the CPU 59 gives the graphic display controller 56 a command which can turn off the entire perspective images G1 and the unlock direction image G3. As a result, since the graphic display controller 56 eliminate the graphic data g1 and g3 stored in the display memory 57, the graphic images G1 and G3 will be disappeared from the monitor 53a of the display unit 53.

The processing will then be returned to the main program shown in FIG. 5.

In the above-mentioned constitution and processing, a processing portion of the main controller 55 correspoding to Steps 62 to 69 in FIG. 5 forms a judging means of the present invention. A processing portion of the main controller 55 correspoding to Steps 61, 71 and 72 in FIG. 5 is in cooperation with the drive motors 24 to 27 and 37 to 39 to form an interlocking means of the present invention. A processing portion of the main controller 55 correspoding to Steps 61, 71, 73 and 74 in FIG. 5 and all Steps in FIGS. 6 and 7 is in cooperation with the graphic display controller 56, the display memory 57, the display interface 58, and the display unit 53 to form a teaching means of the present invention. A processing portion of the main controller 55 correspoding to Step 80 in FIG. 6 forms a deciding means of the present invention. A processing portion of the main controller 55 correspoding to Steps 81 and 82 in FIG. 6 forms a converting means and a graphic data generating means (a first and a second means included) of the present invention. Furthermore, a processing portion of main controller 55 correspoding to all Steps in FIG. 8 forms a color giving means of the present invention.

The above processing may give some examples of unlock operation.

Under normal working state, an operator can give his or her instructions to the controller 50 through the swich board 52. The main cotroller 55 then send drive signals to the driving motor 24 (to 27) or 37 (to 39), thus controlling the various positions of the movable elements at the operator's will for radiographing.

Now let us assume that the spot-film device 21 is set at a limit position prohibited from further movement in the up direction C (refer to a reference character I in FIG. 1). Under this positioning, assume that the operator give an instruction to the operating switch 52a so that the X-ray tube 30 tilts in the obleque-foot side B. This tilting instruction is taken in by the CPU 59 to specify the operation and to drive the corresponding motor 37 of the X-ray tube tilting mechanism (refer to Steps 62 to 67). Immediately after this driving command, the position signal, which is detected by the spot-film device position sensor 51d, is also taken in by the CPU 59 to see if interlock mechanism should be worked (refer to Steps 68 and 69). Since the position sensor 51d indicates that the spot-film device 21 reaches to the limit positon, further move of the X-ray tube 30 for the oblique-foot side B will cause overflow of X-rays outside the tabletop 22. Therefore, to gain an interlock, the x-ray tube tilting mechanism is stopped to move further (i.e. interlocked), and the sub-programs for the interlocked state are started (refer to Steps 69 to 74).

In the processing of the sub-program in FIG. 6, based on a calculated unlock direction, the CPU 59 send the graphic display controller 56 a command so as to display a set of corresponding graphic interlock information as a result, a set of an entire perspective image G1, an interlock-alarming image G2 and an unlock direction image G3 is displayed on the monitor 53a as shown in FIG. 3. The operator can learn, on the interlock-alarming image G2, that interlock is worked for the moving the table 20 and the tabletop 22 (i.e. the X-ray tube 31 is prohibited from moving in the oblique-foot side B), and further can learn easily, on the combination of the entire perspective image G2 and the unlock direction image G3, that moving the spot-film device 21 toward the down direction D will lead to unlock from this interlocked state. Hence, the operator is going to be guided to operate the operating switch 52d into a side which commands the movement of the spot-film device 21 in the down direction D.

Figure 7:
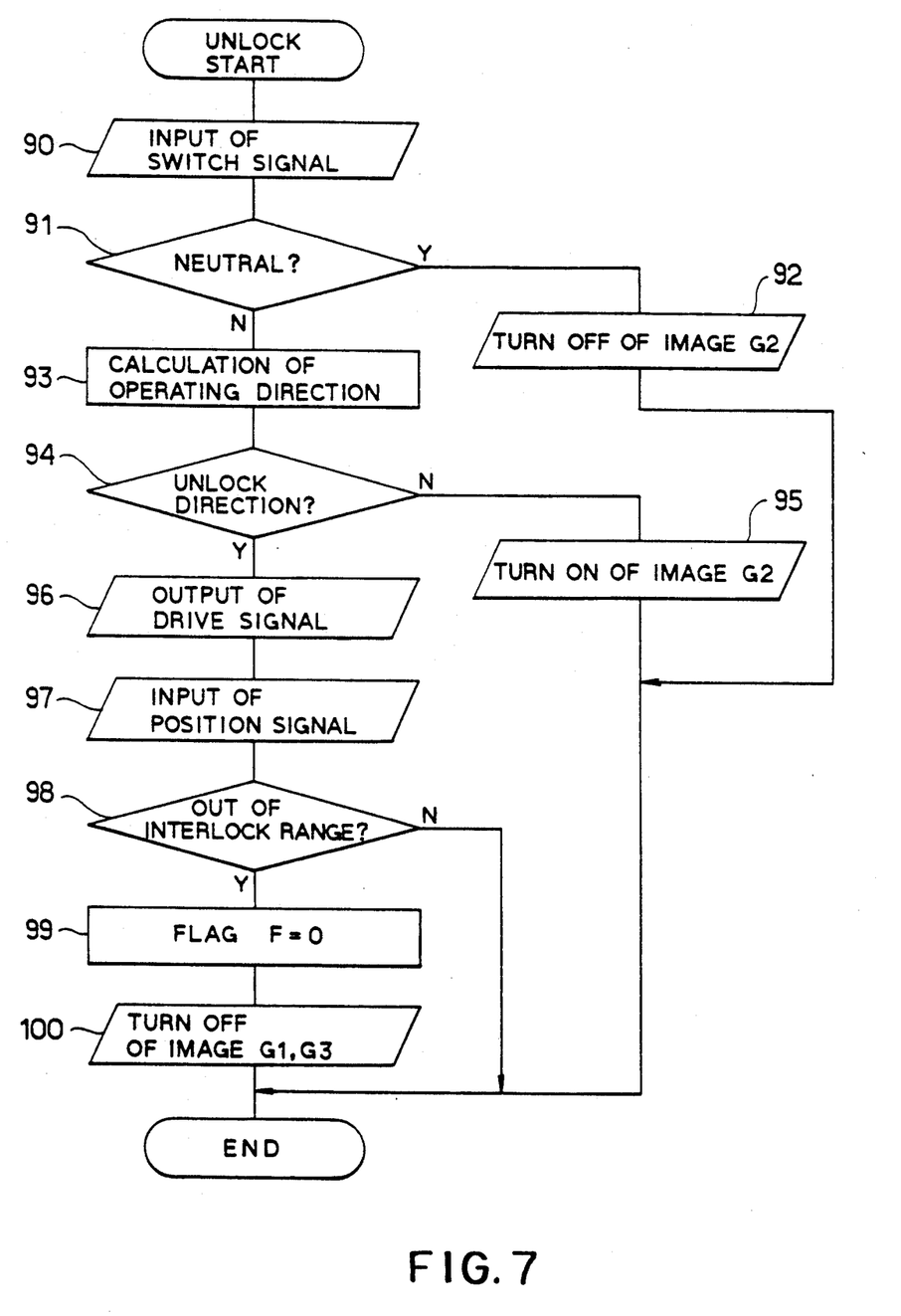

Then, as the operator release the operating switch 52d, the swich position will be returned to its neutral, and the interlock-alarming image G2 will be turned off (refer to Steps 90 to 92 in FIG. 7). However, when the operator gives a command in the opposite direction C, the interlock-alarming image G2 will surely be turned on again with holding the interlocked state (refer to Steps 94 and 95 in FIG. 7).

The operator should necessarily operate the opereting switch 52d so that the spot-film device 21 is moved in the down direction D. Thus, when the spot-film device 21 is moved over a predetermined distance from the present position in that direction D, the interlocked state is unlocked to return to the previous normal working state and all the images G1 and G3 or G1 to G3 are turned off. After this unlock, the x-ray tube 31 can be tilted in the oblique-foot side B.

A next example according to the present embodiment is as follows. Let us assume that tabletop 22 is positioned at a limit in the left direction F. Under this positioning, if an operator selects the radiographic format of a big-square full through the operating switch 52h, interlock mechanism will be worked, because a part of rails guiding the tabletop 22 will come into an X-ray irradiation field from the x-ray tube 31 (refer to Step 62, 63, 66 to 69, 71, 72). Thus, the graphic interlock information consisting of images G1 to G3 is displayed as shown in FIG. 4 to teach the operator the interlocked state about the X-ray exposure and how to unlock from the interlocked state (refer to FIG. 6). Then, as the operator operates the operatging switch 52f so that the tabletop 22 is moved to a certain distance in the right direction E, the interlocked state is unlocked and the images G1 to G3 will be turned off (refer to FIG. 7).

In addition to the above unlock, under the interlocked state, if the operator selects another radiographic format, such as a big-square but divided, by which the part of the rails does not come into the X-ray irradiation field, it is possible to unlock and to turn off the images G1 to G3.

As a result, the graphic interlock infomation can be given to an operator according to contents of the interlocked states. This information can distinctively teach the operater which operating switch should be operated and to which way the operating switch should be moved for unlocking. The operator can understand contents of those images at a glance, leading to highly improved operation in time and to a reduced operation load.

By the way, in this first embodiment, the processes of Steps 91 and 92 in FIG. 7 can be omitted to simplify the unlock sub-program.

A second embodiment of the present invention will now be explained with FIGS. 8 and 9. For the same components as the first embodiment, the same reference numerals are used in this embodiment.

In this second embodiment, the display unit 53 is designed to be able to display images in different colors. The interlock memory 60 of the main controller 55 stores a wide variety of display patterns. The display patterns are made up of different combinations of moved portions for unlocking and the unlock directions. An image G1' of a moved portion (e.g. the X-ray unit 30, the compression cone 33, and the tabletop 22), a part of the entire perspective image G1 of this apparatus 1, is specified in a different color from the entire perspective image G1, but the same as the unlock direction images G3.

Figure 8:
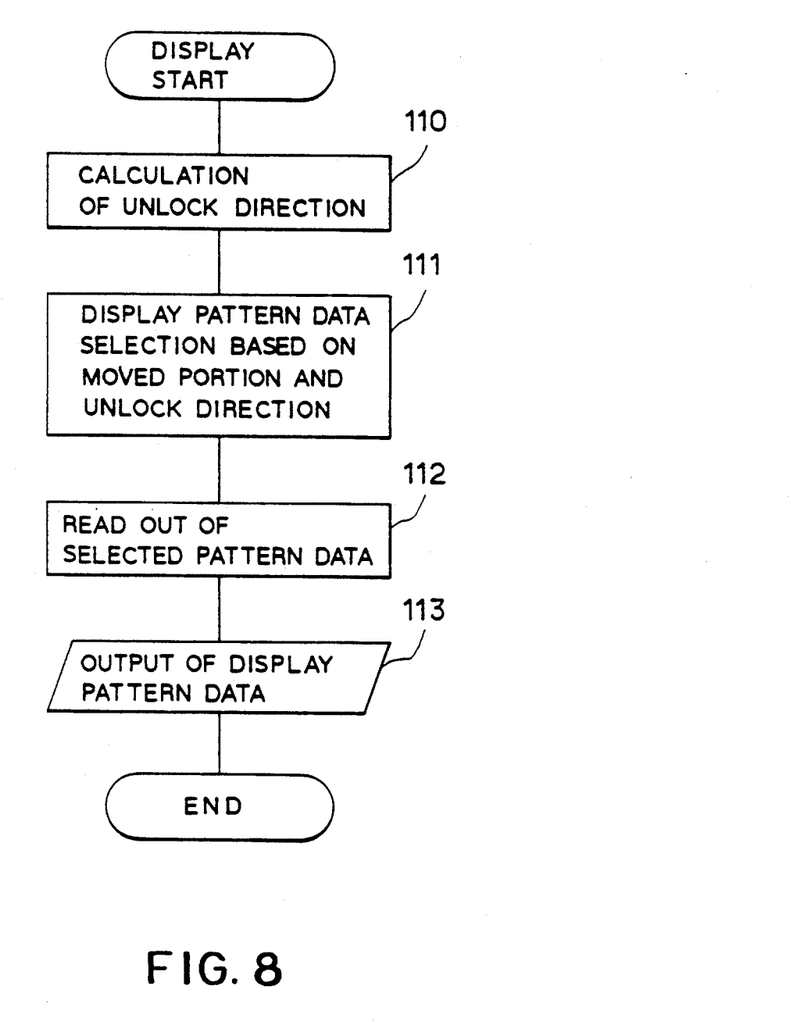
FIG. 8 is a flowchart performed by a controller in a second embodiment.
Figure 9:
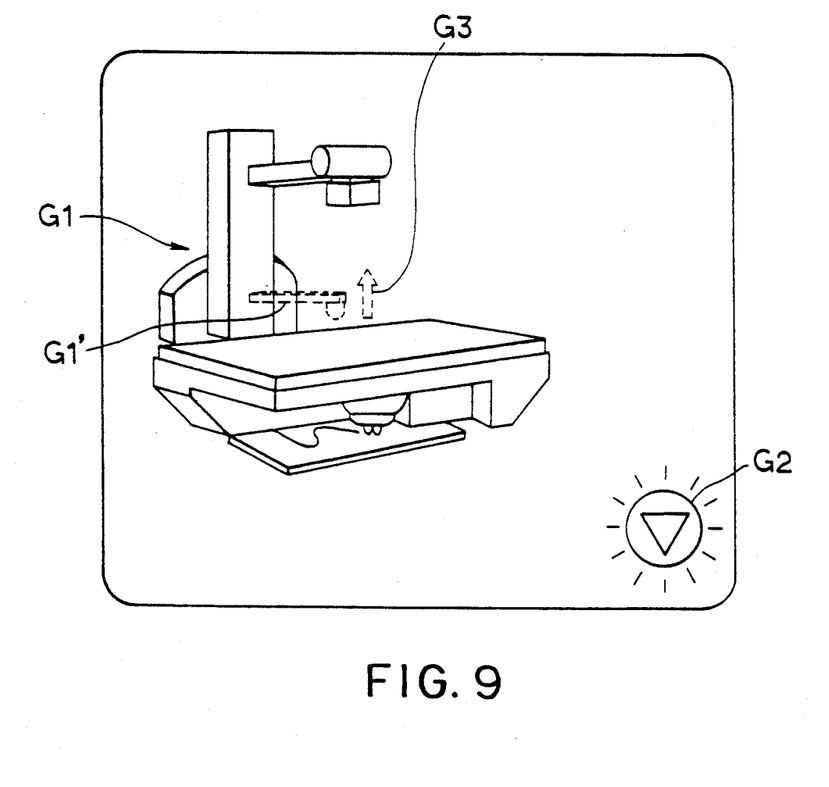
FIG. 9 is an illustration of an example of graphic interlock information displayed on a monitor in the second embodiment.

The main controller 55 is perform processes shown in FIG. 8 instead of the processes in FIG. 6, in addition to the processes in FIGS. 5 and 7.

Especially, at Step 69 in FIG. 5, an moved portion for unloking is also determined.

At first Step 110 in FIG. 8, the unlock direction is calculated. Then at Step 111, based on the moved portion and unlock direction, a display pattern data is selected from the display patterns stored in the interlock memory 60. At Step 112, the selected display pattern data is read out from the interlock memory 60. Finally, at Step 113, the read-out display pattern data is outputted to the graphic display controller 56.

As a result, the second embodiment can provide the equivalent function to the above-mentioned first embodiment. Moreover, a display on the monitor 53a under an interlocked state can be shown like FIG. 9, for instance. In FIG. 9, the compression cone 33 (its arm 33a included) as a moved portion image G1' is directied by an arrow G3 for the front direction (upward in FIG. 9) and the compression cone 33 and the arrow are painted the same color, for example, red in the entire background G1 of green, for example. The moved portion image G1' and the arrow image G3, which are red-painted, are shown, for convenience' sake, by dotted lines in FIG. 8. Therefore, the operator can noticeably recognize Which moved portion should be operated in the apparatus 1, thus leading to more quick operation and to avoiding mis-operation, which may provide a higher efficiency in operation.

In this second embodiment, it may be possible to adopt different colors for a moved portion image G1' and an unlock direction image G3 as long as the moved portion image G1' is painted differnt colors from the entire perspective image G1 of the apparatus 1.

What we claim is:

1. An X-ray radiographing apparatus in which at least one movable element is disposed to be moved for X-ray radiographing in response to commands from a switch means used by an operator, said X-ray radiographing apparatus comprising:

means for detecting positions of said movable element;

means for judging whether or not said movable element is positioned in a predetermined interlock range in response to signals from said switch means and said detecting means;

means for interlocking said movable element when judgement by said judging means shows that said movable element is positioned in the interlock range;

means for teaching the operator an interlocked state of the movable element and how to unlock the interlocked state with graphic images, when said interlocking means begins working.

2. An X-ray radiographing apparatus as claimed in claim 1, wherein said teaching means comprises means for deciding an unlock direction of the movable element from the interlocked state when said interlocking means begins working, means for converting the unlock direction decided by said deciding means to a corresponding graphic data, means for generating a graphic data showing the interlocked state of said movable element, and means for displaying combined graphic images corresponding to the graphic data supplied by said converting means and said generating means.

3. An X-ray radiographing apparatus as claimed in claim 1, wherein said teaching means comprises means for deciding an unlock direction of the movable element from the interlocked state when said interlocking means begins working, means for converting the unlock direction decided by said deciding means to a correspoding graphic data, first means for generating graphic data showing the interlocked state of said movable element, second means for generating graphic date showing an entire perspective view of said X-ray radiographing apparatus, and means for displaying combined graphic images corresponding to the graphic data supplied by said converting means and said first and second generating means.

4. An X-ray radiographing apparatus as claimed in claim 3, wherein said at least one movable element comprises a table system having a table.

5. An X-ray radiographing apparatus as claimed in claim 4, wherein the graphic image displayed by said displaying means in response to the graphic data generated by said first generating means is an interlock-alarming image representing the interlocked state resulted from movement of the table.

6. An X-ray radiographing apparatus as claimed in claim 5, wherein the interlock-alarming image is formed by a symbolized mark.

7. An X-ray radiographing apparatus as claimed in claim 3, wherein said at least one movable element comprises an X-ray exposure system.

8. An X-ray radiographing apparatus as claimed in claim 7, wherein the graphic image displayed by said displaying means in response to the graphic data generated by said first generating means is an interlock-alarming image representing the interlocked state for X-ray exposure of the X-ray exposure system.

9. An X-ray radiographing apparatus as claimed in claim 8, wherein the interlock-alarming image is formed by a symbolized mark.

10. An X-ray radiographing apparatus as claimed in claim 3, wherein said the graphic image displayed by said displaying means in response to the graphic data converted by said converting means is formed by an arrow image representing the unlock direction.

11. An X-ray radiographing apparatus as claimed in claim 3, wherein said the graphic image displayed by said displaying means in response to the graphic data converted by said converting means is formed by an arrow image representing the unlock direction and at least one abbreviated letter representing the unlock direction.

12. An X-ray radiographing apparatus as claimed in claim 3, further comprising:
   means for giving different colors to the graphic images in response to the graphic data generated by said first and second generating means.

13. An X-ray radiographing apparatus as claimed in claim 12, wherein said color giving means is formed so as to give a same color to the graphic images in response to the graphic data generated by said converting means and said first generating means.

* * * * *

UNITED STATES PATENT AND TRADEMARK OFFICE
CERTIFICATE OF CORRECTION

Page 1 of 3

PATENT NO. : 5,177,778
DATED : 01/05/93
INVENTOR(S) : TSURUMAKI ET AL

It is certified that error appears in the above-identified patent and that said Letters Patent is hereby corrected as shown below:

Column 2, line 18, "data" should be --date--.

Column 3, line 13, "lies" should be --lay--;

line 48, "frong" should be --front--.

Column 4, line 1, "obleque-head" should be --oblique-head--;

line 36, "Of" should be --of--;

Column 7, line 18, "elimitates" should be --eliminates--;

line 67, "correspoding" should be --corresponding--.

Column 8, line 3, "correspoding" should be --corresponding--;

line 8, "correspod-" should be --correspond- --;

line 11, "correspoding" should be --corresponding--;

line 15, "correspoding" should be --corresponding--;

line 30, "obleque-foot" should be --oblique-foot--.

UNITED STATES PATENT AND TRADEMARK OFFICE
CERTIFICATE OF CORRECTION

PATENT NO. : 5,177,778
DATED : 01/05/93
INVENTOR(S) : TSURUMAKI ET AL

It is certified that error appears in the above-identified patent and that said Letters Patent is hereby corrected as shown below:

Column 8, line 30, "obleque-foot" should be --oblique-foot--.

Column 9, line 6, "operet-" should be --operat- --;

line 13, "x-ray" should be --X-ray--;

line 22, "x-ray" should be --X-ray--;

line 28, "operatging" should be --operating--;

line 66, "perform" should be --performing--.

Column 10, line 2, "unloking" should be --unlocking--;

line 24, "Which" should be --which--;

line 31, "differnt" should be --different--.

Column 11, line 1, "correspoding" should be --corresponding--;

line 4, "date" should be --data--;

UNITED STATES PATENT AND TRADEMARK OFFICE
CERTIFICATE OF CORRECTION

PATENT NO. : 5,177,778
DATED : January 5, 1993
INVENTOR(S) : Tsurumaki, et. al.

It is certified that error appears in the above-indentified patent and that said Letters Patent is hereby corrected as shown below:

Column 12, line 7, delete "the";
line 12, delete "the".

Signed and Sealed this

Twenty-sixth Day of April, 1994

Attest:

BRUCE LEHMAN

*Attesting Officer*  *Commissioner of Patents and Trademarks*